Figure 1:
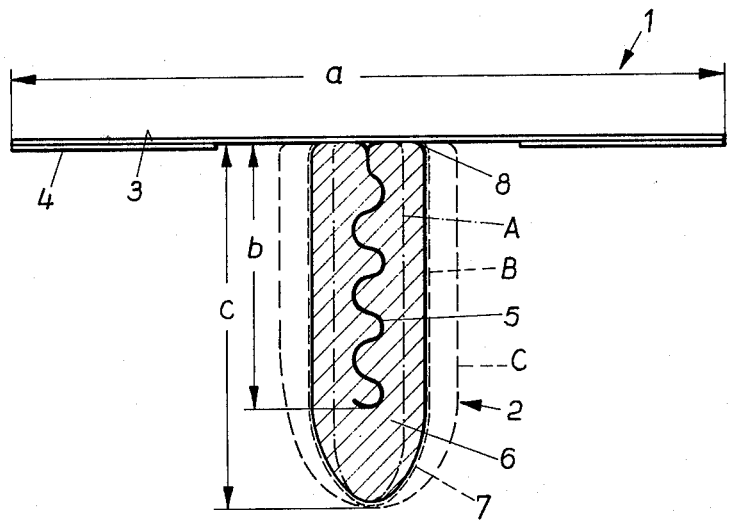

United States Patent [19]
Schenk

[11] 3,958,556
[45] May 25, 1976

[54] CLOSURE MEANS FOR ARTIFICIAL RECTAL OPENINGS

[76] Inventor: Wolfgang Schenk, 111 Rheinstrasse, 62 Wiesbaden, Germany

[22] Filed: July 18, 1974

[21] Appl. No.: 489,601

[30] Foreign Application Priority Data
July 14, 1973    Germany............................ 2335858

[52] U.S. Cl................................. 128/1 R; 128/270
[51] Int. Cl.²......................................... A61B 19/00
[58] Field of Search.................. 128/1 R, 127–131, 128/260, 263, 267–271, 283–287, 290 R, 290 H, 294, DIG. 23, DIG. 25, DIG. 26

[56] References Cited
UNITED STATES PATENTS

| | | | |
|---|---|---|---|
| 467,599 | 1/1892 | Abundi et al. | 128/270 |
| 1,561,020 | 11/1925 | Pond | 128/270 |
| 1,711,294 | 4/1929 | Weitzner | 128/294 |
| 1,897,423 | 2/1933 | Ferri | 128/270 |
| 1,977,133 | 10/1934 | Linard | 128/285 |
| 2,243,529 | 5/1941 | Grossman et al. | 128/1 R |
| 2,931,353 | 4/1960 | Kitzul | 128/1 R |
| 3,083,704 | 4/1963 | Swearingen | 128/283 |
| 3,537,454 | 11/1970 | Gordon | 128/271 |
| 3,804,091 | 4/1974 | Nolan et al. | 128/283 |

Primary Examiner—John D. Yasko
Attorney, Agent, or Firm—Strauch, Nolan, Neale, Nies & Kurz

[57] ABSTRACT

Device for the temporary closing of artificial anus consisting essentially of a flexible synthetic plastic sheet carrier adopted to be adhesively attached directly to the skin of the user, a mounting pin projecting from ashesive coated side of the carrier, and an absorbent tampon on the mounting pin adapted to be inserted into the lumen of the anus. Different sizes of tampons may be selectively mounted on the pin, as at the time of use of the device.

7 Claims, 2 Drawing Figures

CLOSURE MEANS FOR ARTIFICIAL RECTAL OPENINGS

This invention concerns a device for the temporary closing of an artificial anus with a flexible closing plug to be introduced into the lumen of the intestine with the artificial anus and a flanged abutment which is to be placed on the outside of the body of the user, normally on the abdominal wall.

Devices of this kind have become known, in which the closing apparatus comprises a partially inflexible outer part and a flexible inner part, constructed like a type of air pillow (U.S. Pat. Nos. 2,564,399 and 3,447,533). The inflexible portion of the closing plug penetrates through the muscular abdominal wall, at an abutment placed on the outside of the body of the user, while the flexible portion of the closing plug is radially expanded behind the abdominal wall in the lumen of the intestine, to fasten the device in the artificial anus.

For the radial expansion of the flexible closing plug portion, it was suggested that the closing plug should be contracted axially by means of a chain, a cord or springs (U.S. Pat. No. 3,447,533).

It has also been suggested however, that the flexible portion of the closing plug be constructed as a type of elastic bubble made of rubber or similar material, which can be inflated from the outside by means of a rubber balloon (U.S. Pat. No. 2,564,399). A relatively complicated technical construction is required for these known devices in order to effect the radial expansion in inserted closing plugs. Consequently, these known devices are technically complicated and particularly susceptible to soiling and unintentional loosening, and, especially for older persons who in the main use artificial anuses because of cancer of the large intestine, the mechanism is difficult to handle. Moreover, the artificial anus cannot be adequately closed with these familiar devices, especially with regard to intestinal gases and liquids, which temporarily deform the closing plug portion which is flexible and expands radially and press through to the outside, past the more or less inflexible closing plug portion. The devices known from these patents are permanent devices and as a result are rather nauseating during the necessary cleaning procedures.

Tightly fitting pelots (Pelotten) or attached plastic bags are still being used in practice. These possibilities are, however, highly inadequate. To close the artificial anus, an enormous effort is necessary to press the familiar pelots by means of a pelot girdle. Besides the fact that the use of such pelots is quite uncomfortable, it may cause a curvature of the intestinal membranes which can lead to bleeding and infection. In addition, the pelots can be displaced from the artificial anus by body movements, so that it lies open. The familiar plastic bags which can be fastened are suitable and intended only for collecting, not for actually retaining intestinal gases. Since persons equipped with the artificial anus have no possibility of retaining feces and intestinal gases by their own free will, and since the transfer of feces and intestinal gases into the plastic bag can cause both rather loud sounds and a strange odor in the feces, the user of such plastic bags is subject to a severe social handicap even under most favorable circumstances. Furthermore, the attached bag has the disadvantage that the partially filled plastic bag is a nuisance and can incidentally lead to a situation in which the attached bag unintentionally detaches from the skin of the user, especially in the summer, when he perspires. Here, too, the wearing of a girdle is recommended.

In contrast, the invention is based on the principle of considerably improving devices of the type described above, for temporarily closing the artificial anus with a closing plug and abutment part in such a manner as to guarantee the maximum requirements of cleanliness and simple usage, combined with a comfortable fit and realiable closure.

In the invention, this novel result is obtained by constructing the closing plug for one-time use as a type of tampon made of absorbent material, and constructing the abutment portion as a leakproof circular elastic carrier part for the closing plug which is fastened to the skin of the user.

The combination of the absorbent closing plug and the circular elastic carrier part, which is leakproof and fastened to the skin of the user, ensures an absolutely hermetic closure of the artificial anus without the necessity of pressing any rigid parts against the body in the region of the artificial anus (as in U.S. Pat. Nos. 2,564,399 and 3,447,533). Moreover, the device in conformity with the invention has a specially simple construction and inexpensive production possibilities. In addition, the closing plug, constructed as a type of tampon made of absorbent material to be used only one, improves considerably the conditions for maintaining the artificial anus clean.

The devices known from said patents are too inflexible on the outside for the muscular stomach wall of the user, and the inner closing support is too soft for a secure fit. In the invention, the entire closing apparatus is flexible and adjustable to the stomach wall, fitting tightly on the inside and outside.

The carrier part can be constructed as a disk of a physiologically harmless artificial material such as polyvinylchoride, having a layer of an adhesive that is agreeable to the skin on the side which faces the body of the user and containing in its center portion the support for the closing plug. The adhesive layer, agreeable to the skin, provides a completely tight closing that is totally leakproof with regard to gases and liquids. This adhesive on the carrier portion can in itself effect the secure fastening of the closing device. The user has, however, the option of using, in addition, an abdominal bandage or, for women, a girdle, which does not exert an uncomfortable or harmful pressure.

Within the scope of the invention, the circular carrier portion and the closing plug can be connected permanently or temporarily. The circular carrier part can carry, in the center portion of the area facing the body of the user, a helical support plug for a soft closing plug like a tampon. Since the carrier part and closing plug can be separated, it is possible to connect these two parts just before the device is used. The connected parts can be removed together after use. In special cases, it is also possible to use the carrier part several times and the disposable tampon-type closing plug connected thereto only once.

The closing device according to the invention can be adjusted to all lumen sizes of the artificial anus. The disk-shaped carrier part can thus be of the same size in substantially all cases while the closing plug is constructed in different diameters, with a length of approximately 6 centimeters.

Figure 2:
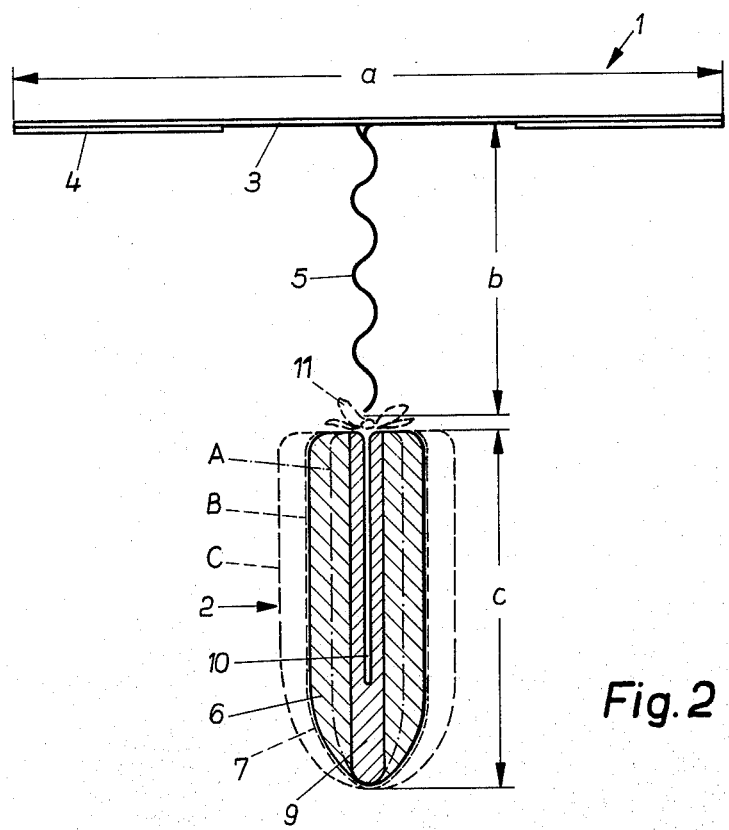

The two construction examples of the invention are explained in detail in the following by means of diagrams:

FIG. 1 shows in cross-section a preferred construction type of the device in conformity with the invention, and FIG. 2 shows in cross-section a construction type of the device in conformity with the invention, in which the carrier part and closing plug are separate and can be connected afterwards.

In the example of FIG. 1, the support or carrier part 1 and the closing plug 2 are connected with one another from the outset. The carrier part 1 consists of a sheet-like element in the form of a circular disk 3 with a diameter $a$ of approximately 12 centimeters and a thickness of from about 0.2 to about 1 millimeter(s). The disk 3 in this example is of polyvinylchloride and carries, on the side which faces the body of the user, an annular cover or coating 4 made of a non-irritating adhesive agreeable to the skin and which will adhere to the skin. In the center portion, which is free from adhesive material, a helical connecting pin structure 5 is tightly attached to disk 3. The axial length $b$ of this connecting pin 5 amounts to about 5 centimeters, while the axial length $c$ of the closing plug 2 is about 6 centimeters.

The closing plug 2 preferably consists essentially of a band of width $c$ made of flexible absorbent cotton material 6, wound around the helical connecting pin 5 and drawn over the coils. A cover 7 of textile gauze is placed over the cotton winding 6 to hold the connecting plug and cotton together; and this cover is closed at the front of the closing plug 2 and at the back part, i.e. at disk 3, it is drawn more tightly together at 8 to guarantee a firm, secure support on the helical connecting pin 5. As shown by the dashed line and by the line of alternate dots and dashes, the connecting plug may be constructed in different diameters to fit different lumen sizes of the artificial anus. The dash-and-dot line shows the size of a connecting plug [A] approximately 1 centimeter in diameter. The solid line shows the size of a connecting plug of about 2 centimeters diameter [B], and the dashed line represents the size of closing plug c [i.e. C], with a diameter of about 3 centimeters.

In the example of FIG. 2, the support part 1 and the closing plug 2 are designed for later connection usually at the time of use; and this can be of special advantage with regard to packing and in the choice of the closing plug size. The carrier part 1, with its diameter $a$, disk 3, adhesive layer 4 and connecting pin with axial length $b$, are constructed substantially as a unit in the same manner as described above in connection with FIG. 1. In this example, the closing plug 2 contains in its center portion, if necessary, a more rigid core 9 which retains its stiffness even when damp and around which the cotton layers 6 are wound. As shown in FIG. 2, the core 9 can have an axial bore 10 to serve as a guide for the helical connecting pin 5. The gauze cover 7, surrounding the closing plug, is closed at the front end of the closing plug 2 and fastened together at the back end at 11. As in the example of FIG. 1, the closing plug 2 in this construction type can be constructed in different diameters: A (1 centimeter diameter), B (2 centimeters diameter), C (3 centimeters diameter); preferably, however, the axial length $c$ should always be the same (6 centimeters).

For use according to the example of FIG. 2, the helical connecting pin 5 of the carrier part 1 is inserted into the core 9 of the closing plug 2 like a corkscrew until the parts in assembly are substantially as in FIG. 1.

The actual use is then the same in both species of the invention. The device is introduced by inserting closing plug 2 into the lumen of the intestine of the artificial anus and the adhesive area 4 of the carrier part 1 is pressed onto the skin area surrounding the artificial anus, after first removing any protective foil. Adhesive 4 may be a well known pressure sensitive type of adhesive. Proper insertion of plug 2 effects a tight closure of the artificial anus. In order to release feces and intestinal gases, the closing device is removed, so that a completely controlled removal of feces and gases can be carried out and the user is in no way socially handicapped by annoying sounds and smells. In the example of FIG. 1 the entire closing device is disposed of after a single use. In the example of FIG. 2, the user has the choice of disposing, after use, of either the complete connected closing device or only the closing plug 2.

In both constructions, the adhesive layer 4 is preferably equipped with a protective cover (not shown in the diagram) made of untearable paper or plastic foil, which provides protection during transport and storage and which is removed immediately before use, to avoid sticking together and to keep the adhesive layer fresh.

The protective cover may extend approximately 5 millimeters beyond the rim of the circular carrier part 1 and is cut radially on at least one point of its circumference to guarantee the uncomplicated removal of the cover.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by Letters Patent is:

1. Device for the temporary closing of an artificial anus, comprising a flexible closing plug which is adapted to be introduced into the lumen of the artificial anus and a flangetype abutment portion which is adapted to be placed on the outside of the body adjacent the anus, generally on the abdominal wall of the user; the characteristics of which device are:

a. that the said abutment portion is a leakproof carrier in the form of a flexible synthetic plastic sheet having on the side that is to face the body an annular region of adhesive material agreeable to the human skin and adapted to hold the device in place on the user's body while sealing against escape of fluid from the anus, and a projecting generally helical mounting pin, said flexible sheet and said mounting pin being connected together as a unit; and b. that the said closing plug is in the form of a tampon of absorbent material of suitable size mounted on said pin to complete the assembly for use, and the said closing plug has a core of firmer material than the tampon surrounding it, said pin being screwed into said core in assembling the device for use.

2. Device as per claim 1 characterized in that said carrier is essentially circular and approximately 12 centimeters in diameter, while the closing plug is about 6 centimeters long and may have an initial diameter in the range of 1–3 centimeters.

3. Device as per claim 1 characterized in that the mounting member is shorter than the closing plug so that the tampon covers the inner end thereof.

4. Device as claim 1 characterized in that the area of the carrier which is adapted to face the body and adhere to it is covered for safe transport and storage with a protective shield which is removed prior to use of the device.

5. Device as defined in claim 1 wherein said adhesive is of the pressure sensitive type.

6. The device defined in claim 1 wherein said element is a disc of polyvinylchloride.

7. Device for the temporary closing of an artificial anus, comprising a flexible closing plug which is adapted to be introduced into the lumen of the artificial anus and a carrier for said plug containing a sheet-like element of physiologically harmless synthetic material such as polyvinylchloride adapted to be placed on the outside of the body around the anus, generally on the abdominal wall of the user, and having a coating of an adhesive that is agreeable to the human skin for fastening and sealing said element to the skin of the user, and a supporting member for said closing plug in the form of a generally helical pin to connect said element to said closing plug, said supporting member being substantially centrally fastened to said element and being adapted to project substantially centrally into said closing plug, and said closing plug comprising a tampon of absorbent material surrounding a core of firmer material than the tampon and said pin being introduced into said core for assembling the device for use.

* * * * *